United States Patent [19]

Hawiger et al.

[11] Patent Number: 4,666,884

[45] Date of Patent: May 19, 1987

[54] METHOD OF INHIBITING BINDING OF VON WILLEBRAND FACTOR TO HUMAN PLATELETS AND INDUCING INTERACTION OF PLATELETS WITH VESSEL WALLS

[75] Inventors: Jack J. Hawiger, Chestnut Hill; Sheila Timmons; Marek Kloczewiak, both of Boston, all of Mass.

[73] Assignee: New England Deaconess Hospital, Boston, Mass.

[21] Appl. No.: 598,711

[22] Filed: Apr. 10, 1984

[51] Int. Cl.$^4$ .............................................. A61K 37/43
[52] U.S. Cl. ........................................ 514/13; 514/17
[58] Field of Search ................. 260/112.5 R; 435/214; 424/22; 514/13, 17

[56] References Cited

U.S. PATENT DOCUMENTS

| 4,303,592 | 12/1981 | Laura et al. | 435/214 |
| 4,351,337 | 9/1982 | Sidman | 424/22 |
| 4,455,290 | 6/1984 | Olexa et al. | 260/112.5 R |
| 4,476,116 | 10/1984 | Anik | 260/112.5 R |

OTHER PUBLICATIONS

Biochemistry, 1982, vol. 21, No. 6, pp. 1414–1420—Isolation, Characterization and Synthesis of Peptides from Human Fibrinogen that Block the Staphylococcal Clumping Reaction and Construction of a Synthetic Particle.
Biochemical and Biophysical Research Communications, vol. 107, No. 1, Jul. 16, 1982, pp. 181–187—Localization of a Site Interacting with Human Platelet Receptor on Carboxy-Terminal Segment of Human Fibrinogen Chain.
Thrombosis Research 29; 249–255, 1983—Fibrinogen Site for Platelets.
"Localization of a Fibrin α-Chain Polymerization Site Within Segment Thr-374 to Glu-396 of Human Fibrinogen", Proc. Natl. Ac. Sci. (USA) 81, pp. 5980–5984 (1984).

*Primary Examiner*—Delbert R. Phillips
*Attorney, Agent, or Firm*—Lahive & Cockfield

[57] ABSTRACT

A method of inhibiting von Willebrand factor binding to human platelets induced with thrombin, ADP, or other stimuli has been developed. The administration of the small molecular weight peptide or the synthetic inhibitory molecule of the invention significantly inhibits thrombin or ADP-modified human platelets binding of von Willebrand factor, a plasma protein necessary for platelet interaction with blood vessels. The method of the invention is useful for inhibiting the formation of hemostatic platelet plugs and the initiation of thrombotic lesions. The blockage caused by hemostatic platelet plugs and the damage caused by thrombotic lesions are major factors in heart disease and stroke. The invention also includes a method of inducing the interaction of platelets with blood vessels by administration of a synthetic platelet reactive molecule.

17 Claims, 1 Drawing Figure

METHOD OF INHIBITING BINDING OF VON WILLEBRAND FACTOR TO HUMAN PLATELETS AND INDUCING INTERACTION OF PLATELETS WITH VESSEL WALLS

The invention described herein was made, in part, in the course of work under research grants numbers HL-30649 and HL-30648, from the National Institutes of Health, U.S. Public Health Service.

BACKGROUND OF THE INVENTION

The present invention relates to interaction of human platelets with blood vessels mediated by von Willebrand factor. More particularly, the invention relates to a method of inhibiting thrombin or ADP-induced binding of von Willebrand factor to human platelets as well as the construction of a synthetic molecules capable of initiating the adhesion reaction linking human platelets to blood vessels.

A number of different mechanisms have been disclosed which lead to the initiation of blood clots (thrombi). One such mechanism is the thrombin or ADP-induced platelet binding of the multivalent molecules, fibrinogen or von Willebrand factor. Thrombin or ADP induce modification of the platelet structure, allowing interaction between the platelets and fibrinogen to form aggregates and binding of von Willebrand factor by the platelets to initiate adhesion or linking to blood vessels. Von Willebrand factor is also involved in the ristocetin-induced aggregation (clumping) of platelets. While the exact mechanisms are not clear, one theory is that thrombin, ADP or ristocetin cause stereochemical changes in the glycoproteins of the platelet cell membrane. The stereochemical changes create receptor sites on the platelet so that platelet binding regions on the fibrinogen or von Willebrand factor molecules can react with the receptor site. Until recently, the mechanisms of binding of human fibrinogen or von Willebrand factor to human platelets were unknown. In 1982, Hawiger, Timmons, Kloczewiak, Strong and Doolittle demonstrated that the primary fibrinogen interaction site with human platelets is located on the gamma chain of fibrinogen. See Proc. Natl. Acad. Sci. USA 79:2068-2071 (1982). In a later paper, Kloczewiak, Timmons and Hawiger demonstrated that the platelet binding region was contained within the carboxyl terminal 27 peptide residues of the gamma chain and that a 15 peptide carboxyl terminal fragment of this molecule could block fibrinogen platelet aggregation. See Biochem. and Biophy. Rsc. Comm. 107:181-187 (1982). In 1982 Fujimoto, Ohara, and Hawiger, and Fujimoto and Hawiger described the interaction between ristocetin, thrombin, or ADP-modified platelets and von Willebrand factor molecules. See J. Clin. Invest. 69: 1212-1222 (1982); Nature (London) 297: 154-156 (1982).

Both fibrinogen and von Willebrand factor are important in the formation of hemostatic platelet plugs and initiation of thrombotic lesions. Blockage caused by these plugs and the damage caused by thrombotic lesions are major factors in heart disease and stroke. Much research has been directed toward developing drugs which will dissolve already formed blood clots but most of these drugs have not been particularly effective. Recently, reports on the use of tissue plasminogen activator, a molecule which modifies circulating plasminogen molecules to form plasmin, an enzyme that dissolves blood clots, have been given much publicity. While enzymatic methods of dissolving clots may help minimize the after effects of heart attacks, a pharmaceutical preparation which will inhibit platelet adhesion prior to occlusion of the blood vessels may prevent the initial blockage responsible for cardiac or cerebral infarction.

Alternatively, molecules promoting platelet adhesion to blood vessels may have a variety of uses. For example, a number of patients, e.g., some bleeders, may be lacking von Willebrand factor due to a genetic deficiency or due to excessive consumption in circulation. A synthetic platelet adhesion promoting molecule can assist in platelet plug formation and attachment of plugs to blood vessels to arrest bleeding and help these patients to lead normal lives.

Accordingly, an object of the invention is to develop a method of inhibiting platelet binding of von Willebrand factor promoted by thrombin, ADP or other stimuli. Another object of the invention is to provide a molecule which promotes platelet interaction with blood vessels. A further object of the invention is to provide a synthetic molecule which inhibits platelet binding of von Willebrand factor with significant circulation time in the blood stream. These and other objects and features of the invention will be apparent from the summary, the drawing and the description.

SUMMARY OF THE INVENTION

The present invention features a method of inhibiting binding of von Willebrand factor to human platelets. The invention also features a series of synthetic molecules which promote or inhibit interaction of human platelets with blood vessels.

In particular, the method of invention includes the step of incubating human platelets with a peptide having a carboxyl terminal sequence Lys-X-X-X-Asp-X-COOH where each X is individually selected from a group consisting of naturally occurring acids. Preferably, the carboxyl terminal sequence is Lys-Gln-Ala-Gly-Asp-Val-COOH.

Incubation of the platelets with thrombin or ADP may be prior to or simultaneous with the peptide incubation. In one embodiment, thrombin or ADP-induced binding of von Willbrand to human platelets is inhibited by the incubation of the platelets with a peptide having 6-14 residues containing this carboxyl terminal sequence. In another embodiment, infusion of the peptide causes inhibition of platelet-blood vessel interaction as measured by prolongation of time required to arrest the bleeding in an experimental model of blood vessel injury. Preferably, the peptide is a dodecapeptide having the sequence H$_2$N-His-His-X-X-X-X-Lys-X-X-X-Asp-X-COOH where each X is individually selected from a group consisting of amino acids. Most preferably, the dodecapeptide has the sequence H$_2$N-His-His-Leu-Gly-Gly-Ala-Lys-Gln-Ala-Gly-Asp-Val-COOH.

The invention further features a method for inhibiting thrombin or ADP-induced binding of von Willebrand factor to human platelets by incubating human platelets with a synthetic molecule having the carboxyl terminal sequence

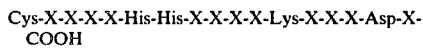
Cys-X-X-X-X-His-His-X-X-X-X-Lys-X-X-X-Asp-X-COOH where each X is individually selected from a group consisting of amino acids. The inhibition of platelet-von Willebrand factor binding inhibits adhesion of the platelets to blood vessels. Preferably, the synthetic molecules has the sequence

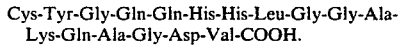
Cys-Tyr-Gly-Gln-Gln-His-His-Leu-Gly-Gly-Ala-Lys-Gln-Ala-Gly-Asp-Val-COOH.

In one embodiment, human platelets are incubated with a cystinyl-linked dimer of this heptadecapeptide while in another embodiment, the synthetic molecule consists of this heptadecapeptide grafted to a polymeric backbone, e.g., a protein, most preferably human serum albumin, at a ratio such that each polymer molecule contains not more than one heptadecapeptide. This synthetic peptide-polymer has a longer inhibitory effect because it is not as easily cleared from the blood stream.

The invention also features a method of promoting interaction of human platelets with blood vessels in the absence of von Willebrand factor by incubating the platelets with a synthetic adhesion-promoting molecule. This method includes the step of incubating the platelets with a molecule formed of a plurality of peptides having the carboxyl terminal sequence

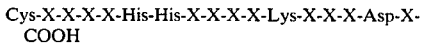
Cys-X-X-X-X-His-His-X-X-X-X-Lys-X-X-X-Asp-X-COOH grafted to a polymeric backbone. Each X is individually selected from a group consisting of amino acids. Preferably, the synthetic molecule has the sequence

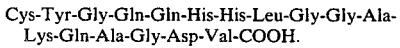
Cys-Tyr-Gly-Gln-Gln-His-His-Leu-Gly-Gly-Ala-Lys-Gln-Ala-Gly-Asp-Val-COOH.

The preferred polymeric backbone is a protein, most preferably human serum albumin.

BRIEF DESCRIPTION OF THE DRAWING

The sole FIGURE of the drawing illustrates the inhibition of ADP-modified platelet binding of von Willebrand factor caused by incubation with a peptide of the invention.

DESCRIPTION

Figure 1:
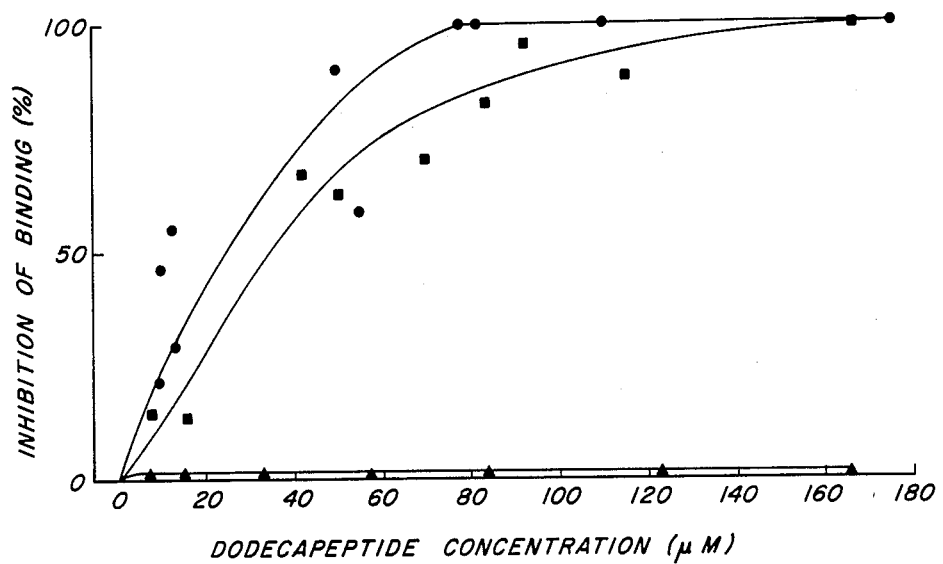

The present invention is based, in part, on the discovery that a primary attachment site on the fibrinogen molecule in the thrombin or ADP-induced fibrinogen aggregation of human platelets is located in the twelve carboxyl terminal residues of the gamma chain. Surprisingly, the same dodecapeptide which inhibits aggregation of fibrinogen and platelets also inhibits thrombin or ADP-induced binding of von Willebrand factor to human platelets. One possibility for this phenomenom is that the thrombin or ADP-modified platelets have a binding site for von Willebrand factor which has a similar stereochemical structure as the fibrinogen site. These discoveries provide the basis for a method of inhibiting binding of von Willebrand factor to human platelets induced with thrombin, ADP, or other stimuli as well as providing the basis for the fabrication of molecules which can promote or inhibit interaction of platelets with blood vessels.

The synthetic peptides described herein were synthesized in a manual shaker apparatus (Chipco Manufacturing) following the solid phase procedure of Barany and Merrifield described in *The Peptides Analysis, Synthesis, and Biology* (Gross and Meinhoper, Eds.), Vol. 2, pp. 1–284 (Academic Press, 1980). An aminomethyl resin (0.45 M/g) was derivatized with tertbutoxycarbonyl ("Boc")-Val-(4-oxymethyl) phenylacetic acid. The general solid phase synthesis protocol uses the following chemicals: 50% trifluoracetic acid ("TFA") for deprotection, 5% triethylamine for neutralization and a 2–3 fold excess of preformed Boc-amino acid symmetric anhydrides for couplings except for glutamine and histidine residues where direct dicylcohexylcarbodiimide coupling was used. The level of resin substitution, completeness of coupling, and deprotections were measured by quantitative ninhydrin reactions. The protecting groups and the peptide-resin link were cleaved by reaction in liquid HF/anisole (9:1 v/v) for one hour at 0° C. After evaporation of the HF, the resin was washed twice with ninhydrin ethylether, and crude peptides were extracted with 10% acetic acid and freeze-dried. These lyophilized peptides were dissolved in 10% acetic acid, the insoluble material was removed by filtration, and the peptides were purified by high pressure liquid chromotography (HPLC) using a Beckman 430 chromatograph and Whatman preparative column. The absorbed peptide was eluted from the column with 0.1% (w/v) TFA until absorbancy at 214 nm returned to the base line, then a linear gradient of acetonitrile, from 0 to 80% concentration with 0.1% TFA, was applied for 100 minutes. The main peptide peak was collected and freeze dried.

Cysteine-containing peptides were converted to cystine cross-linked peptides by oxidation with the potassium ferricyanide. The cysteine-containing peptide was dissolved in 0.2 M Tris-HCl buffer, pH 7.4, at approximately 10 mg/ml and was mixed with a 2 M excess of potassium ferricyanide and incubated at room temperature for 2 hours. After acidification, the peptide was mixed with AGIx8 (Bio Rad) resin to remove inorganic reagents and the supernatent was rechromatographed on an analytical column. The resulting main peptide peak was collected and freeze dried.

The synthetic adhesion promoting molecule was formed by dissolving 10 mg/ml human serum albumin (Miles Laboratories) in 0.1 M $Na_2HPO_4$ and mixing the albumin with a 10-fold molar excess of 17.9 mM N-succinimidyl (p-azidophenyldithio) propionate (Pierce) in dioxane to introduce additional sulfhydryl residues in the albumin. The reaction was carried out at 4° C. in the dark for one hour before the mixture was dialyzed, in the dark, against several changes of distilled water containing 1 mM mercaptoethanol and then against water. A 10-fold molar excess of the heptadecapeptide containing the cysteinyl terminal residue was added to the modified albumin in 0.05 M Tris-HCL buffer and free sulfhydryl residues were oxidized with potassium feracynanide. After oxidation, the whole mixture was acidified to pH 3 with acetic acid and mixed for a few minutes with AGI x 8 resin. The resin was centrifuged and the supernatent dialyzed against 0.15 M sodium chloride. To form the albumin linked inhibitory molecule, the 10-fold excess of the cysteinyl peptide was replaced by 1:1 molar ratio of the cysteinyl peptide to albumin.

The following nonlimiting Example illustrate the efficiency of the invention. This Example uses the reagents formed by the procedures delineated above.

EXAMPLE 1

This Example illustrates that the method of the invention can be used to inhibit binding of von Willebrand factor to ADP-treated human platelets. FIG. 1 illustrates the level of inhibition of $^{125}$I-von Willebrand factor binding to ADP-modified human platelets by incubation with a synthetic dodecapeptide H$_2$N-His-His-Leu-Gly-Gly-Ala-Lys-Gln-Ala-Gly-Asp-Val-COOH.

The FIGURE also illustrates that the same dodecapeptide does not inhibit the binding of $^{125}$I-von Willebrand factor to risocetin-modified human platelet.

Specifically, FIG. 1 shows that addition of various levels of the dodecapeptide to $10^8$ human platelets/0.55 ml treated with 5 μM of ADP five minutes prior to the addition of 14 μg of $^{125}$I-labelled von Willebrand factor (■ - ■) or 33 μg of $^{125}$I-labelled fibrinogen (● - ●) will cause substantial binding inhibition. The FIGURE also shows that the dodecapeptide does not inhibit the binding of $^{125}$I-labelled von Willebrand factor to human platelets treated with 0.6 mg/ml ristocetin (▲ - ▲).

One explanation for these results is that the binding of the dodecapeptide to the ADP-modified human platelets prohibits binding of fibrinogen or von Willebrand factor by sterically blocking the protein binding site. However, the ristocetin-modified human platelets are not hindered in binding von Willebrand factor. This experiment suggest ristocetin causes a different modification of the platelets than ADP or thrombin so that von Willebrand factor binds to ristocetin-modified platelets through a different binding site than it does to ADP or thrombin treated platelets. These experiments indicate that distinct binding domains on von Willebrand factor can participate in its binding to human platelets modified with thrombin, ADP, or ristocetin. Small peptides analogous to these domains can block one or two binding sites responsible for interaction of von Willebrand factor with platelets.

A potential problem with the use of small peptides as a method of preventing interaction between platelets and von Willebrand factor is that small peptides are cleared from the bloodstream in a very short time. By conjugating the synthetic peptides to human serum albumin at a concentration of no more than one peptide per albumin molecule, a larger, hopefully more stable, platelet adhesion inhibitory molecule can be formed.

The foregoing description is purely illustrative and other skilled in the art may determine other modifications or variations of the method and products of the invention. Such other modifications or variations are included within the following claims.

What is claimed is:

1. A method for inhibiting binding of von Willebrand factor to human platelets comprising the step of treating human platelets with a synthetic peptide analog of the platelet receptor recognition site of von Willebrand factor which contains 6-14 residues having a carboxyl terminal sequence Lys-X-X-X-Asp-Val-COOH where each X is individually selected from a group consisting of amino acids.

2. The method of claim 1 wherein said synthetic peptide analog has the carboxyl terminal sequence Lys-Gln-Ala-Gly-Asp-Val-COOH.

3. The method of claim 1 wherein said synthetic peptide analog is a dodecapeptide having the sequence H$_2$N-His-His-X-X-X-Lys-X-X-X-Asp-Val-COOH where each X is individually selected from a group consisting of amino acids.

4. The method of claim 3 wherein said synthetic peptide analog peptide has the carboxyl terminal sequence H$_2$N-His-His-Leu-Gly-Gly-Ala-Lys-Gln-Ala-Gly-Asp-Val-COOH.

5. The method of claim 1 wherein said inhibition of von Willebrand factor binding to human platelets inhibits interaction of said platelets with blood vessels.

6. A method of inhibiting binding of von Willebrand factor to human platelets comprising the step of treating human platelets with a molecule having a carboxyl terminal sequence consisting of Cys-X-X-X-X-His-His-X-X-X-X-Lys-X-X-X-Asp-Val-COOH where each X is individually selected from a group consisting of amino acids, where said carboxyl terminal sequence is a synthetic peptide analog of the platelet receptor recognition site of von Willebrand factor.

7. The method of claim 6 wherein said molecule has the carboxyl terminal sequence Cys-Tyr-Gly-Gln-Gln-His-His-Leu-Gly-Gly-Ala-Lys-Gln-Ala-Gly-Asp-Val-COOH.

8. The method of claim 6 wherein said molecule comprises a cystinyl-linked dimer of said carboxyl terminal sequence.

9. The method of claim 7 wherein said molecule comprises a cystinyl-linked dimer of said carboxyl terminal sequence.

10. The method of claim 6 wherein said molecule comprises said carboxyl terminal sequence grafted to a carrier molecule backbone in a proportion such that each carrier molecule backbone contains no more than one of said synthetic peptide analogs having this carboxyl terminal sequence.

11. The method of claim 10 wherein said carrier molecule backbone comprises a protein.

12. The method of claim 10 wherein said carrier molecule backbone comprises human serum albumin.

13. The method of claim 6 wherein said inhibition of von Willebrand factor binding to human platelets inhibits interaction of said platelets with blood vessels.

14. A method of promoting the interaction of human platelets with blood vessels in the absence of von Willebrand factor comprising the steps of forming an artificial interaction molecule by grafting a plurality of synthetic peptide analogs of the platelet receptor recognition site of von Willebrand factor to a carrier molecule backbone, each of said synthetic peptide analogs having the carboxyl terminal sequence, Cys-X-X-X-X-His-His-X-X-X-X-Lys-X-X-X-Asp-Val-COOH where each X is individually selected from a group consisting of amino acids;

treating said human platelets with said artificial interaction molecule to form a complex; and allowing the human platelet-artificial interaction molecule complex to interact with said blood vessels.

15. The method of claim 14 wherein each synthetic peptide analog has the carboxyl terminal sequence Cys-Tyr-Gly-Gln-Gln-His-His-Leu-Gly-Gly-Ala-Lys-Gln-Ala-Gly-Asp-Val-COOH.

16. The method of claim 14 wherein said carrier molecule backbone comprises a protein.

17. The method of claim 14 wherein said carrier molecule backbone comprises human serum albumin.

* * * * *